United States Patent [19]
Tsai

[11] Patent Number: 6,080,991
[45] Date of Patent: Jun. 27, 2000

[54] METHOD FOR MILLING A TRANSMISSION ELECTRON MICROSCOPE TEST SLICE

[75] Inventor: Ching-Long Tsai, Taipei, Taiwan

[73] Assignee: United Microelectronics Corp., Hsinchu, Taiwan

[21] Appl. No.: 09/135,495

[22] Filed: Aug. 17, 1998

[30] Foreign Application Priority Data

Jun. 18, 1998 [TW] Taiwan ................................ 87109768

[51] Int. Cl.⁷ .................................................. H01J 37/26
[52] U.S. Cl. ...................................... 250/492.21; 250/309
[58] Field of Search .............................. 250/492.21, 311, 250/307, 309, 310

[56] References Cited

U.S. PATENT DOCUMENTS

| | | | |
|---|---|---|---|
| 5,525,806 | 6/1996 | Iwasaki et al. | 250/492.21 |
| 5,656,811 | 8/1997 | Itoh et al. | 250/492.21 |
| 5,770,861 | 6/1998 | Hirose et al. | 250/492.21 |

*Primary Examiner*—Kiet T. Nguyen
*Attorney, Agent, or Firm*—Thomas, Kayden, Horstemeyer & Risley

[57] ABSTRACT

A focused ion beam (FIB) is used to mill a test slice to form an observable wall for a transmission electron microscope (TEM). A slanting angle θ of the observable wall surface is automatically formed. The method for milling the test slice includes the following steps: The first step is to measure the slanting angle θ. The next step is to tilt the test slice with the slanting angle θ in both a counterclockwise direction and a clockwise direction and to perform FIB milling so that the TEM observable wall has a uniform thickness. Furthermore, during the FIB milling, an aperture in the TEM observable wall serves as a milling stop signal.

13 Claims, 5 Drawing Sheets

METHOD FOR MILLING A TRANSMISSION ELECTRON MICROSCOPE TEST SLICE

CROSS-REFERENCE TO RELATED APPLICATION

This application claims the priority benefit of Taiwan application serial no. 87109768, filed Jun. 18, 1998, the full disclosure of which is incorporated herein by reference.

BACKGROUND OF THE INVENTION

1. Field of the Invention

This invention relates to a method for milling a test slice, and more particularly to a method of milling a transmission electron microscope (TEM) test slice, which has a uniform thickness.

2. Description of Related Art

In a failure analysis of a vary-large-scale-integration (VLSI) device, the analysis of a cross-sectional surface has been accepted as an effective diagnostic technology. A scanning electron microscope (SEM) is one of the diagnostic tools used to observe the cross-sectional surface but its resolution is poor when integration density is high, as is the case with the VLSI device. The TEM is another diagnostic tool, which has been introduced to gradually replace the SEM. In order to maintain the reliability of the VLSI device and streamline its production, the TEM is becoming more commonly used for damage analyses of VLSI devices.

Because of the application of the TEM, the production of a test slice with an allowed thickness becomes an important issue. Generally, the test slice is kept at a thickness less than 0.25 micron so that electrons from the TEM can travel through it. In light of these considerations, the focused ion beam (FIB) was developed to mill the test slice to a predetermined thickness.

FIG. 1 is a schematic perspective view of a test slice. A whole slice is cut out from a predetermined position and is then re-cut to produce a test slice 100, of a given dimension, as shown in FIG. 1. The test slice 100 has a thickness about 25–35 microns. One example is 30 microns. Using a FIB 102 to mill the test slice 100 from the top and gradually reach the dotted side surface forms a TEM observable wall 104. The thickness of the TEM observable wall 104 should be less than about 0.25 microns as required by a TEM 106, which is applied to diagnose the TEM observable wall 104.

In FIG. 2A, the upper plot is a schematic top view of the test slice in FIG. 1 showing the structure of the test slice 100. The lower plot is a schematic cross-sectional view taken along the line I—I in the upper plot. The shaded region is the region milled by the FIB 102. The TEM observable wall 104 has a thickness "$d_1$", which is less than about 0.25 microns. The method described above is called the one-sided method.

Another method is called the two-sided method, and is similar to the one-sided method. The difference is that, in the two-sided method, both sides are milled as shown in FIG. 2B. In FIG. 2B, the upper plot is a schematic top view of another test slice; the lower plot is a schematic cross-sectional view taken along the line II—II in the upper plot. A TEM observable wall is formed at the middle of the test slice with a thickness of "$d_1$" less than about 0.25 micron.

FIG. 3A is a top view schematically illustrating the conventional milling flow of a TEM test slice. FIG. 3B is a schematic cross-sectional view taken along the III—III line on the FIG. 3A.

In FIG. 3A and FIG. 3B, A1, A2, A3, and A4 correspond to B1, B2, B3, and B4, respectively. In a step A1, a sacrificial layer 310, indicated as a shaded region, is coated on the top surface of a TEM test slice 300, which is shown as the square. The sacrificial layer 310 made of, for example, platinum (Pt) serves as a milling stop signal. In a next step A2, a FIB with a large current roughly mills the TEM test slice. A milling front 320a indicates the place where the FIB milling process has occurred. In a next step A3, a FIB with middle current mills the TEM test slice. A milling front 320b indicates accomplishment of another milling step, which has reached the sacrificial layer 310. Then, in a next step A4, a FIB with small current mills the TEM test slice. A milling front 320c is further formed. The region under the sacrificial layer 310 is a TEM observable wall, which is not uniform in thickness.

FIG. 4 is a schematic drawing of a cross-sectional view in detail, according to FIG. 3B. In FIG. 4, a shaded region represents the sacrificial layer 310 shown in FIG. 3B. A slanted surface 410 of the TEM observable wall is automatically formed due to FIB milling. The slanted surface 410 has a slanting angle θ away from a normal line, which is taken along a normal direction of the top surface of the TEM test slice. The normal line, in fact, is also along a FIB incident direction. The thickness, also called the width, of the TEM observable wall is gradually wider from the top to the bottom. Since the thickness is progressively wider, the thickness around the bottom region may be too thick even though the top region has a suitable thickness. If the thickness is too thick, TEM can not effectively penetrate the TEM observable wall, and then TEM diagnosis is therefore limited only on the top region.

Moreover, the desired thickness of the TEM observable wall is very small, for example, 0.1 microns. Moreover, the desired thickness is based on the milling stop signal, which depends on the residual sacrificial layer 310 shown in FIG. 3A and FIG. 3B after milling. This thickness of 0.1 microns cannot be easily controlled. If over-milling occurs, the test slice is then damaged. On the contrary, if insufficient milling occurs, the test slice is then not suitable for TEM diagnoses. It becomes an important issue to choose a proper type of milling stop signal in order to obtain a TEM test slice with a proper uniform thickness.

SUMMARY OF THE INVENTION

It is therefore an objective of the present invention to provide a method for milling a TEM test slice to have a proper uniform thickness so that the TEM diagnoses can be more efficiently performed on the whole TEM test slice.

It is another an objective of the present invention to provide a method for milling a TEM test slice by using a location of an aperture in a TEM test slice as a milling stop signal to prevent insufficient milling or over milling of the TEM test slice.

In accordance with the foregoing and other objectives of the present invention, a method for milling a TEM test slice includes several steps as follows:

As FIB milling is performed to vertically mill the TEM test slice, a slanted surface of a TEM observable wall is intrinsically formed with a slanting angle. The first step is to figure out the slanting angle, which is between a normal line of the TEM test slice and the slanted surface.

According to the slanting angle θ, next step is to tilt the TEM test slice with a positive angle of +θ and mill it by the FIB. Another similar step follows, with a difference in except a negative angle of −θ, in which the angles +θ and the angle −θ are the incident angle of the FIB onto the TEM test slice surface. These two steps result in a uniform thickness of the TEM test slice. This step is repeated until a desired thickness of the TEM observable wall is met.

BRIEF DESCRIPTION OF DRAWINGS

The invention can be more fully understood by reading the following detailed description of the preferred embodiment, with reference made to the accompanying drawings as follows.

DETAILED DESCRIPTION OF PREFERRED EMBODIMENT

Figure 1:
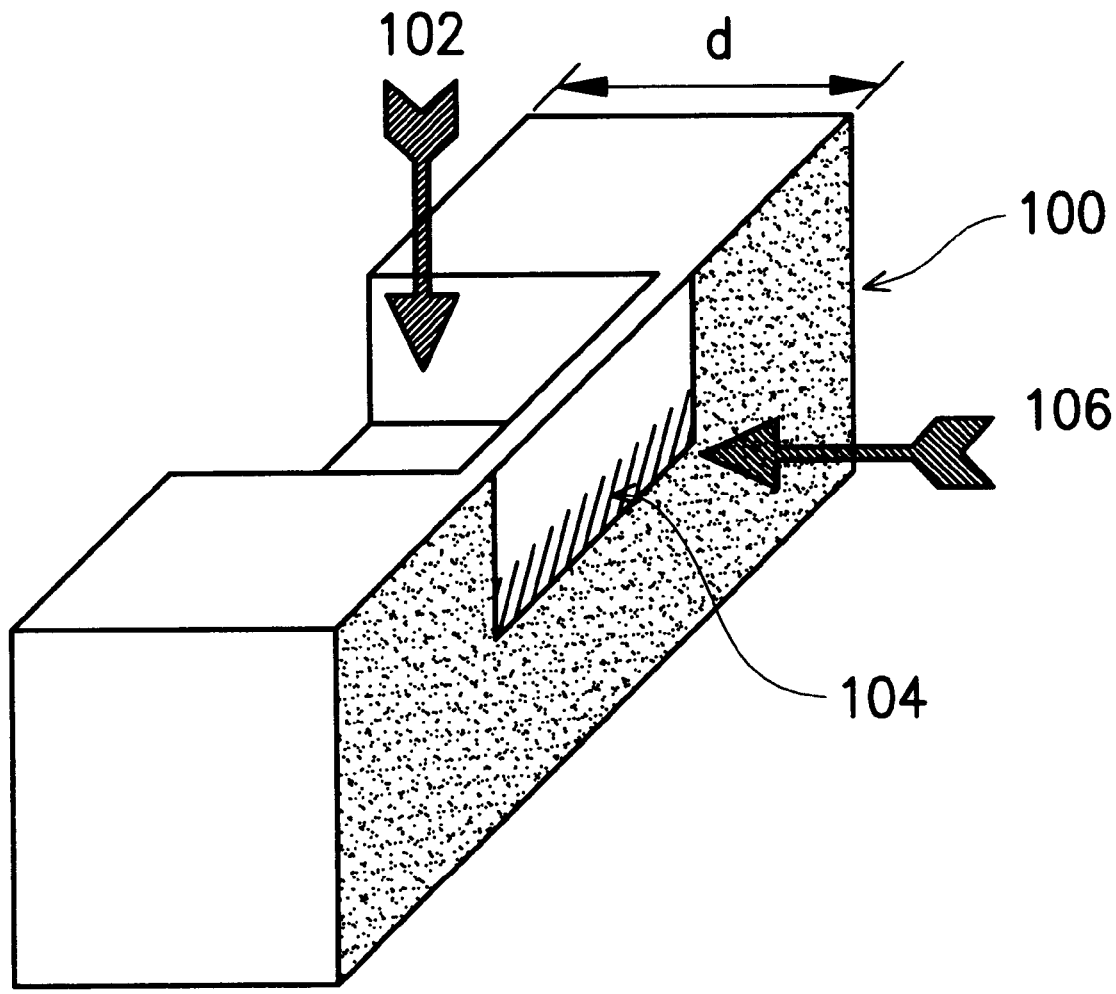
FIG. 1 is a schematic perspective view of a test slice.
Figure 2A:
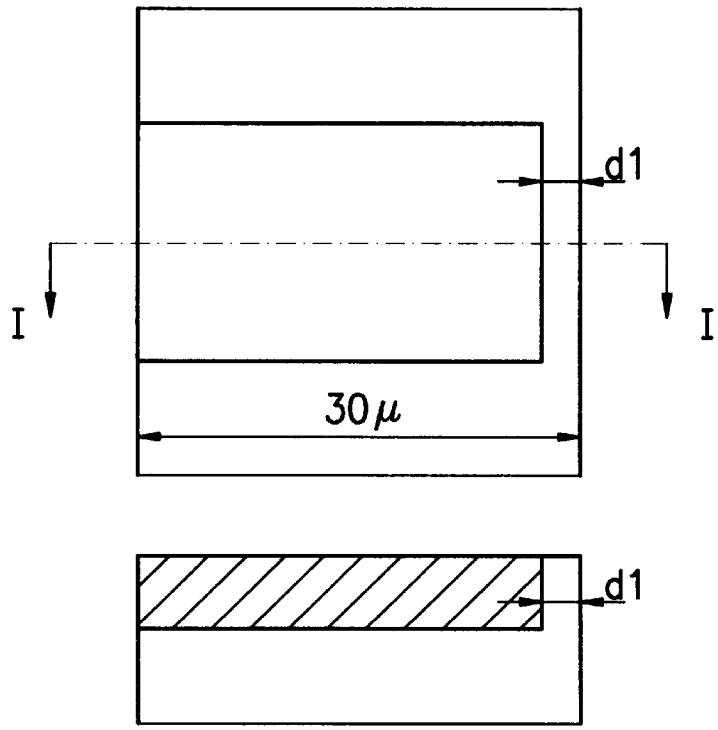
FIG. 2A and FIG. 2B are schematic top and cross-sectional views of two conventional methods for milling a TEM test slice.
Figure 2B:
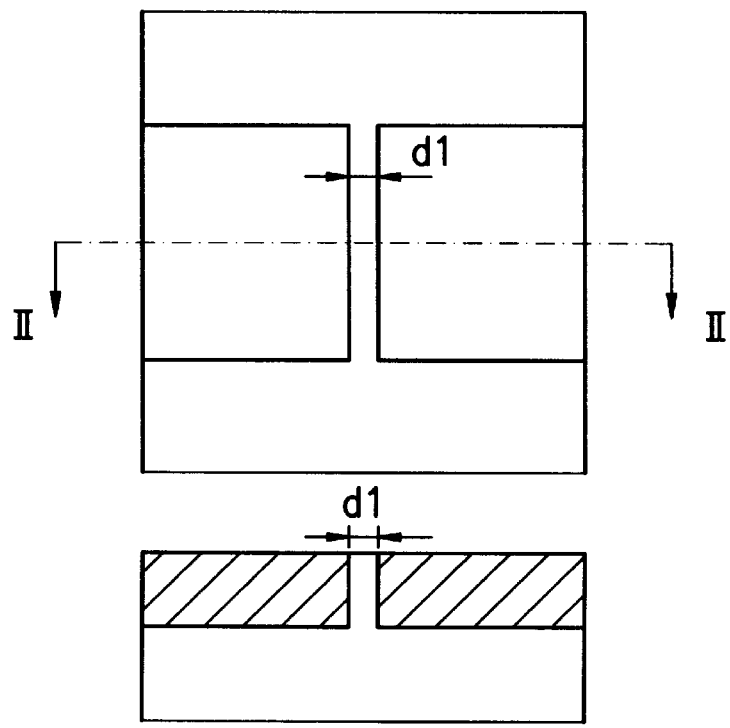
Figures 3A, 3B:
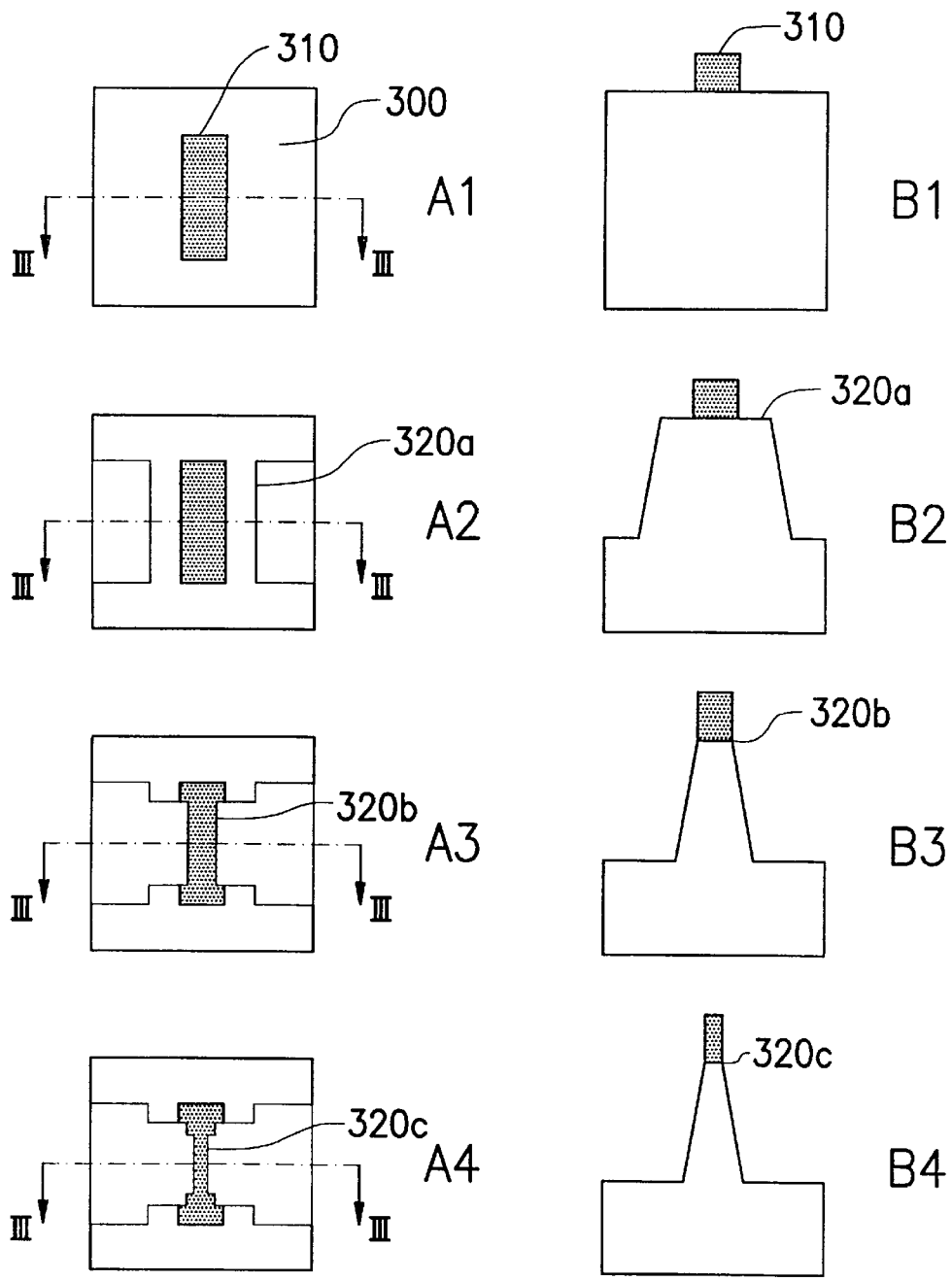
FIG. 3A and FIG. 3B are top and cross-sectional views schematically illustrating a conventional milling flow of a TEM test slice.
Figure 4:
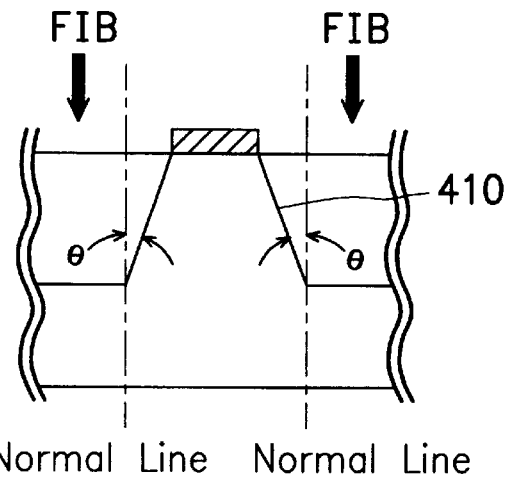
FIG. 4 is a schematic drawing of a cross-sectional view in detail, according to FIG. 3B.

The TEM test slice has an original thickness of about 30 microns. A suitable range can be about 25–35 microns. One can perform the steps shown in FIG. 3A and FIG. 3B until the step A4, at which point a small current of FIB is used to mill the TEM test slice. Then several steps are performed according to the invention. First, at this stage, a slanting angle θ described in FIG. 4 is determined by, for example, measuring it. This slanting angle θ is intrinsic to the FIB milling process.

Figure 5A:
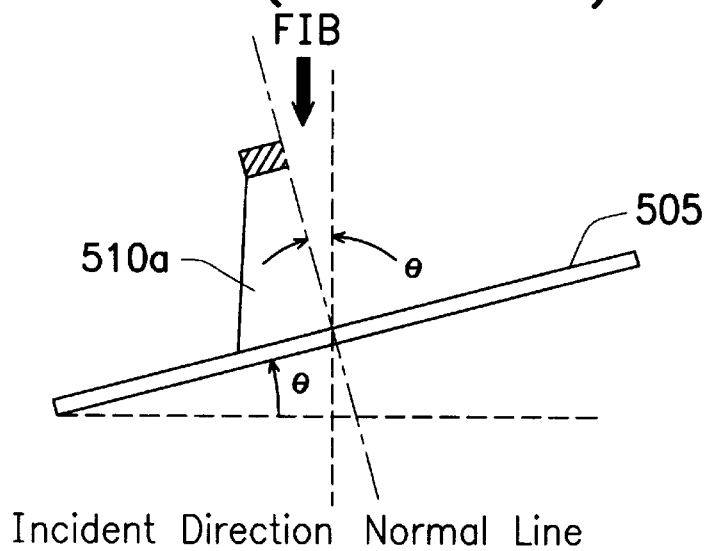
FIG. 5A and FIG. 5B are cross-sectional views schematically illustrating a FIB milling method for a TEM test slice, according to a preferred embodiment of the invention.
Figure 5B:
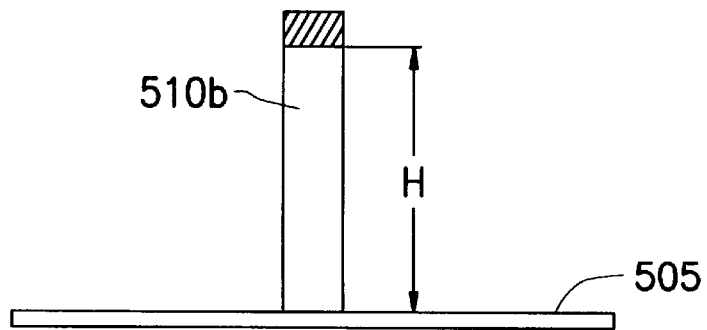

FIG. 5A and FIG. 5B are cross-sectional views schematically illustrating a FIB milling method for a TEM test slice, according to a preferred embodiment of the invention. In FIG. 5A, a working flat plate 505, which is used to hold the TEM test slice, is tilted with an angle θ, also called the tilt angle, substantially equal to the intrinsic slanting angle, in counterclockwise direction. One side surface of a TEM observable wall 510a is thereby parallel to the FIB incident direction. Next, the FIB milling process is performed again to remove a portion of the TEM observable wall on the other side. A FIB incident angle to the working flat plate 505 is exactly the tilted angle θ. Since the intrinsic slanting angle always exists, the TEM observable wall 510a on this side has a surface just normal to the working flat plate 505. In other word, this side surface is parallel to a normal line of the working flat plate 505. For another point of view, the FIB incident angle to the working flat plate 505 is the same as the slanted angle θ so that the FIB just removes a triangular portion to obtain a side surface with the intrinsic slanting angle relative to the FIB incident direction. This results in the TEM observable wall 510a having one surface normal to the working flat plate 505.

Subsequently, a FIB milling process similar to the previous step but with a negative tilt angle of θ is performed so that each side surface of the TEM observable wall 510a become parallel to each other and normal to the working flat plat 505. In FIG. 5B, a TEM observable wall 510b is formed with a uniform thickness, and each side of the observable wall 510b are normal to the working flat plate 505. This step is repeated until a desired thickness is met, in which the desired thickness is determined by a milling stop signal as is to be described in next paragraph. The height H of the TEM observable wall 510b is at least about 20 microns, which is the allowed depth for the invention because the thickness is uniformly and sufficiently thin. For a conventional method, the allowed depth is about 3 to 4 microns because the bottom region of the convention TEM observable wall is too thick as shown in FIG. 3B and FIG. 4.

Figure 6:
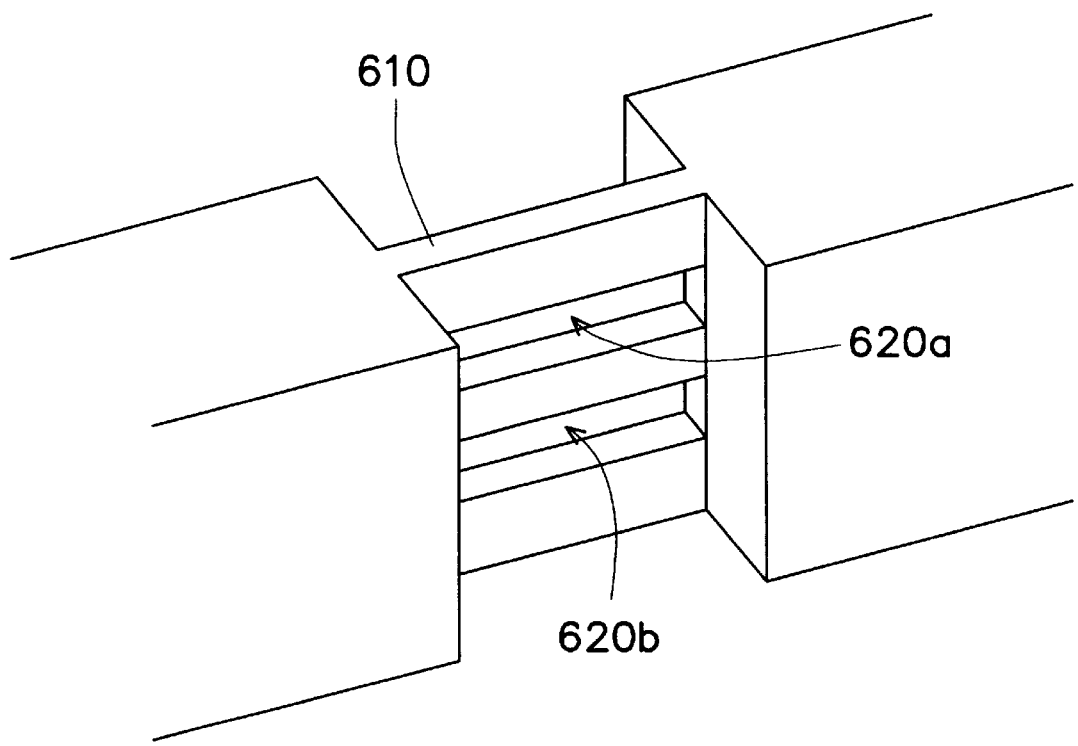
FIG. 6 is a perspective view schematically illustrating a formation of an aperture in the TEM test slice when the incident angle is larger than the intrinsic slanting angle.

As the thickness of the TEM observable wall becomes closer to the observable thickness of, for example, about 0.1 microns, if the incident angle θ of the FIB is larger than the slanting angle of the side surface, then an aperture occurs in the TEM observable wall. This can be understood by referring to FIG. 5A and FIG. 6, which is a perspective view schematically illustrating a formation of an aperture in the TEM test slice when the incident angle is too large. In FIG. 5A and FIG. 6, if the FIB incident angle θ is too large, then the result of milling both sides of the TEM observable wall 610 is the formation of an aperture 620a in the upper region of the TEM observable wall 610. The occurrence of the aperture 620a means that the thickness of the TEM observable wall 610 is close to the TEM observable thickness. Moreover, according to the location of the aperture 620a, the incident angle θ can be adjusted to be a little smaller. In this case, an aperture 620b is formed in the lower region. A lower location of the aperture 620b means that the side surfaces of the TEM observable wall 610 are more parallel. One can repeat adjusting the incident angle θ to attain a desired location of the aperture 620b. If the height H, shown in FIG. 5B, of 20 microns is desired, then the location of the aperture 620b is required to be, for example, 20 microns or more below the top surface of the TEM observable wall 610. The desired thickness of the TEM observable wall is achieved. The location of the aperture 620b therefore serves as a milling stop signal in the invention, in which once the aperture 620b occurs, the thickness is within the observable range for TEM diagnoses.

The aperture 620a occurs when the FIB incident angle θ is too large. If the FIB incident angle θ is too small, then the aperture 620a may not occur. In order to avoid this situation, the FIB incident angle θ can be set to be a little larger than the ideal intrinsic slanting angle, such as few percent larger, to ensure occurrence of the aperture 620a.

In conclusion, the method for milling the TEM test slice of the invention is characterized as follows:

1. The thickness of the TEM observable wall is uniform to increase the observable depth.

2. The aperture in the TEM observable wall is used to adjust the FIB incident angle to achieve the uniform thickness and serves as a milling stop signal to obtain the TEM observable thickness.

The preferred embodiment of the invention as described above is only one of possible examples. The FIB incident direction is fixed in the above example. Of course, one can change the FIB incident direction but maintain the working plate 505 in a fixed position. The FIB can also be replaced by any kind of energetic particle beam (EPB) with similar properties.

The invention has been described using an exemplary preferred embodiment. However, it is to be understood that the scope of the invention is not limited to the disclosed embodiment. On the contrary, it is intended to cover various modifications and similar arrangements. The scope of the claims, therefore, should be accorded the broadest interpretation so as to encompass all such modifications and similar arrangements.

What is claimed is:

1. A method for milling a transmission electron microscope (TEM) test slice by using an energetic particle beam (EPB) to bombard it, the method comprising:

milling the TEM test slice to have a profile with a slanting angle against a normal line;

tilting the TEM test slice by a first tilt angle against a normal line, wherein the first tilt angle is substantial equal to the slanting angle;

milling the TEM test slice to form a first TEM observable wall by adjusting an EPB incident angle onto the TEM test slice, wherein the first TEM observable wall is parallel to the normal line;

tilting the TEM test slice by a second tilt angle against a normal line, wherein the second tilt angle is substantial equal to the slanting angle and in opposite direction of the first tilt angle;

milling the TEM test slice to form a second TEM observable wall by adjusting an EPB incident angle onto the TEM test slice, wherein the second TEM observable wall is parallel to the normal line; and repeating above steps until a desired thickness of the first and the second TEM observable wall is achieved so that the desired thickness is substantially uniform.

2. The method of claim 1, wherein the desired thickness of the TEM observable wall is an observable thickness by the TEM.

3. The method of claim 1, wherein an aperture occurring in the TEM observable wall serves as a milling stop signal, wherein the occurrence of the aperture is due to the EPB incident angle being larger than a slanting angle of a side surface of the TEM observable wall.

4. The method of claim 1, wherein the EPB comprises a focused ion beam (FIB).

5. The method of claim 1, wherein the TEM observable wall comprises a TEM observable thickness and a height at least about 20 microns.

6. The method of claim 1, wherein the TEM observable thickness is about 0.1 micron.

7. The method of claim 1, wherein the TEM test slice comprises a thickness of about 25–35 microns.

8. The method of claim 7, wherein the TEM test slice comprises a thickness of 30 microns.

9. A method for milling a transmission electron microscope (TEM) test slice by using an energetic particle beam (EPB) to bombard it, the method comprising:

milling the TEM test slice to have a profile with a slanting angle against a normal line;

tilting the TEM test slice by a first tilt angle against a normal line, wherein the first tilt angle is substantial equal to the slanting angle;

milling the TEM test slice to form a first TEM observable wall by adjusting an EPB incident angle onto the TEM test slice, wherein the first TEM observable wall is parallel to the normal line;

tilting the TEM test slice by a second tilt angle against a normal line, wherein the second tilt angle is substantial equal to the slanting angle and in opposite direction of the first tilt angle;

milling the TEM test slice to form a second TEM observable wall by adjusting an EPB incident angle onto the TEM test slice, wherein the second TEM observable wall is parallel to the normal line;

reducing the first and the second tilt angle when a first aperture is formed within the TEM test slice; and stopping the milling process when a second aperture is formed within the TEM test slice.

10. The method of claim 9, wherein the EPB comprises a focused ion beam (FIB).

11. The method of claim 9, wherein the first and the second TEM observable walls have a height at least about 20 microns.

12. The method of claim 9, wherein a TEM observable thickness between the first and the second TEM observable walls is about 0.1 micron.

13. The method of claim 9, wherein the thickness of the TEM test slice is about 25–35 microns.

* * * * *